(12) United States Patent
Schachinger

(10) Patent No.: US 9,546,950 B2
(45) Date of Patent: Jan. 17, 2017

(54) OPTICAL GAS SENSING APPARATUS WITH EXPLOSION-PROOF ENCLOSURE

(71) Applicant: Rosemount Analytical Inc., Houston, TX (US)

(72) Inventor: Peter Schachinger, Billdal (SE)

(73) Assignee: Rosemount Analytical Inc., Houston, TX (US)

( * ) Notice: Subject to any disclaimer, the term of this patent is extended or adjusted under 35 U.S.C. 154(b) by 0 days.

(21) Appl. No.: 14/498,309

(22) Filed: Sep. 26, 2014

(65) Prior Publication Data

US 2016/0091418 A1    Mar. 31, 2016

(51) Int. Cl.

| G01N 21/00 | (2006.01) |
|---|---|
| G01N 21/31 | (2006.01) |
| G01N 21/59 | (2006.01) |
| G01N 33/00 | (2006.01) |
| G01N 33/22 | (2006.01) |
| G01N 21/39 | (2006.01) |

(52) U.S. Cl.
CPC .............. *G01N 21/31* (2013.01); *G01N 21/39* (2013.01); *G01N 21/59* (2013.01); *G01N 33/0027* (2013.01); *G01N 33/227* (2013.01); *G01N 2021/399* (2013.01); *G01N 2201/022* (2013.01); *G01N 2201/0236* (2013.01)

(58) Field of Classification Search
CPC .............. G01N 27/16; G01N 2030/025; G01N 2030/8881; G01N 21/3504; G01N 2021/1793; G01N 33/0016; G01N 33/0073; G01N 21/39; G01N 33/0006; G01N 33/0031; G01N 2030/0095; G01N 2030/8804; G01N 30/88
See application file for complete search history.

(56) References Cited

U.S. PATENT DOCUMENTS

| 4,560,875 A | * | 12/1985 | Crowder | ............ G01N 21/3504 250/339.13 |
|---|---|---|---|---|
| 6,006,582 A | * | 12/1999 | Bhandari | ............. G01N 21/783 257/2 |
| 7,864,323 B2 | | 1/2011 | Kluczynski et al. | |

(Continued)

OTHER PUBLICATIONS

Search Report and Written Opinion for International Application No. PCT/US2015/051519, date of mailing: Jan. 13, 2016, date of filing: Sep. 22, 2015, 15 pages.

*Primary Examiner* — Michael P Stafira
(74) *Attorney, Agent, or Firm* — Christopher R. Christenson; Kelly, Holt & Christenson, PLLC

(57) ABSTRACT

An optical gas sensing apparatus includes an explosion-rated device electronics enclosure. An explosion-rated sensing enclosure has a light transmitting element to allow light to pass out of and into the sensing enclosure. The sensing enclosure is operably coupled to the explosion-rated device electronics enclosure by a feed-through. In one aspect, an internal volume of the sensing enclosure is less than or equal to about one fiftieth of the volume of the explosion-rated device electronics enclosure. In another aspect, the thickness of the light transmitting element is less than or equal to about 3 millimeters. A light source is disposed within the sensing enclosure and is operably coupled to the device electronics. A detector is disposed within the sensing enclosure and is also operably coupled to the device electronics.

20 Claims, 2 Drawing Sheets

(56) References Cited

U.S. PATENT DOCUMENTS

| | | | | |
|---|---|---|---|---|
| 8,164,748 B1* | 4/2012 | Flanders | ................. | G01J 3/108 |
| | | | | 356/300 |
| 2006/0093523 A1* | 5/2006 | Norman | ............. | G01N 33/2823 |
| | | | | 422/83 |
| 2006/0243029 A1* | 11/2006 | Lange | .................... | G01N 25/50 |
| | | | | 73/31.05 |
| 2010/0192675 A1* | 8/2010 | Schlichte | ............... | G01N 27/16 |
| | | | | 73/31.06 |
| 2010/0228688 A1* | 9/2010 | Little | .................. | G01N 21/359 |
| | | | | 705/413 |
| 2010/0283991 A1* | 11/2010 | Chrzan | ................. | G01N 21/09 |
| | | | | 356/51 |
| 2014/0036257 A1* | 2/2014 | Kramer | ................. | G01N 21/17 |
| | | | | 356/128 |
| 2014/0124672 A1* | 5/2014 | Stock | .................. | G01N 21/031 |
| | | | | 250/343 |
| 2014/0273263 A1* | 9/2014 | Zanella, Sr. | ........... | G01N 27/16 |
| | | | | 436/149 |
| 2015/0211971 A1* | 7/2015 | Little, III | ................. | G01N 7/14 |
| | | | | 73/64.45 |
| 2016/0041052 A1* | 2/2016 | Fogarty | ................... | G01D 5/28 |
| | | | | 73/744 |

* cited by examiner

US 9,546,950 B2

OPTICAL GAS SENSING APPARATUS WITH EXPLOSION-PROOF ENCLOSURE

BACKGROUND

Gas absorption spectroscopy generally measures the presence and/or concentration of a species of interest in a gas sample by passing a light beam through the sample and detecting the absorption at wavelengths of a particular spectral absorption feature of the species of interest. Generally, such a feature is an absorption line that represents the frequency of light corresponding to vibrational, rotational or electronic transitions of molecules of the gas of interest. Tunable diode lasers provide many advantages for such gas absorption spectroscopy measurements in that the lasers can be tuned to the center of a spectral feature and can provide a relatively narrow signal to the width of the spectral feature.

Laser absorption spectroscopy can thus offer high speed and relatively high precision capabilities in order to detect a variety of trace gas species in gas samples at atmospheric pressures with relatively low cross sensitivity to other gas species or components. Tunable diode laser spectrometers are particularly suited to high sensitivity studies, in part, because they may be frequency modulated to reduce low frequency laser noise and electronic noise. In general, a laser spectrometer will include a frequency tunable laser that generates an illumination output beam that is directed through a sample cell that contains a gas mixture. The beam is then directed to an optical detector and the signal of the detector is demodulated to obtain an absorption-induced signal. This absorption-induced signal can be used to identify one or more species of interest within the gas sample.

SUMMARY

An optical gas sensing apparatus includes an explosion-rated device electronics enclosure. An explosion-rated sensing enclosure has a light transmitting element to allow light to pass out of and into the sensing enclosure. The sensing enclosure is operably coupled to the explosion-rated device electronics enclosure by a feed-through. In one aspect, an internal volume of the sensing enclosure is less than or equal to about one fiftieth of the volume of the explosion-rated device electronics enclosure. In another aspect, the thickness of the light transmitting element is less than or equal to about 3 millimeters. A light source is disposed within the sensing enclosure and is operably coupled to the device electronics. A detector is disposed within the sensing enclosure and is also operably coupled to the device electronics.

DETAILED DESCRIPTION OF ILLUSTRATIVE EMBODIMENTS

Figure 1:
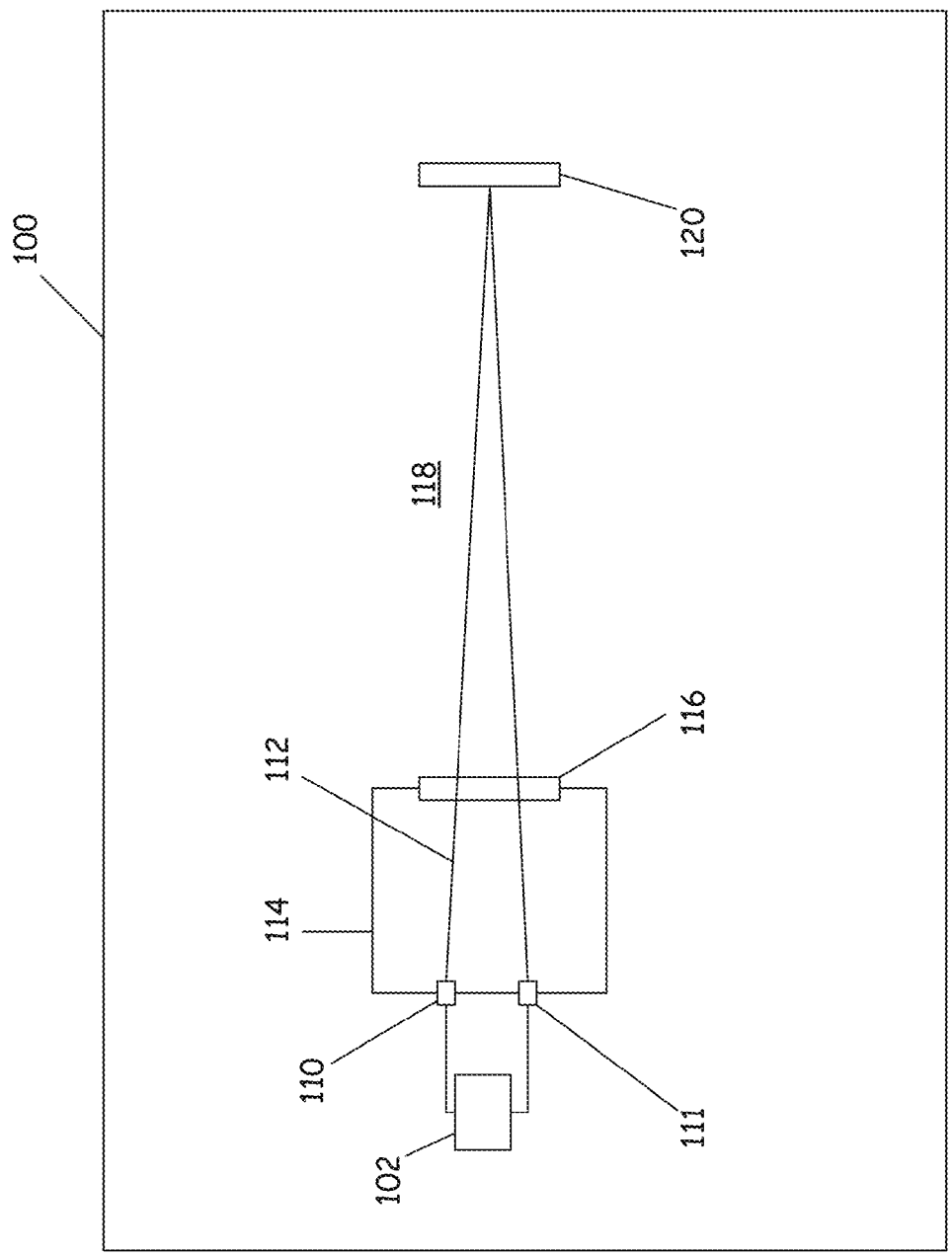
FIG. 1 is a diagrammatic view of a laser spectroscopy system with which embodiments of the present invention are particularly useful.

One challenge for spectroscopic measurements is to control the gas composition in the space outside of the measurement path (i.e., the path between the light source and the measurement path and between the measurement path and the light sensing path). Very small variations of the fluid composition outside the measurement path may affect the measured value and thereby the accuracy of the instrument. One way in which this challenge has been addressed it to enclose the non-measuring optical path in a controlled volume, for example within a hermetic enclosure.

In addition to the challenges above, a measurement path may pass through explosive fluids which must be separated from potential sources of ignition, such as lasers and other electronics. Such components (lasers and other electronics) are generally disposed within an explosion-proof housing, which is strong enough to retain an internal explosion in the event that explosive gases within the enclosure would ignite. Explosion-proof housings can therefore be in contact with the measurement path. When electronics are housed within explosion-proof enclosures, such enclosures can prevent the gases from entering the internal chamber of the enclosure. Additionally, if such gases do enter the enclosure and cause an explosion, the flame will not be able to propagate outside of the enclosure.

One example of an explosion-proof rating is an ATEX certification to Ex d standards EN60079-0 and EN60079-1 for potentially explosive atmospheres. Generally, explosion-proof housings are relatively bulky in order to be mechanically robust enough to contain an internal explosion without rupturing. However, such robust structures can generate challenges for optical-based instruments in which light must pass from a source that could be a potential source of ignition, such as a laser, to a potentially explosive environment. In such instances, the light source, light sensing elements, and the controlled volume described above are generally disposed together inside an explosion-proof housing. Due to the number of components within the housing, the size of the housing—and therefore the internal pressure of any potential explosion—will be of such a magnitude that the element transmitting light into the measurement path will need to be thick enough in order to sustain and contain any potential explosion. However, the thickness of this light transmission element can generate optical disturbances in the measurement.

For example, U.S. Pat. No. 7,864,323 provides a method for measuring the concentration of a gas component in a measuring gas. This patent teaches an arrangement that is amenable to explosion-proof housings. When devices in accordance with the patent are manufactured, the light path has to pass through a relatively thick optical lens. Additionally, the volume between the light source and the lens must be filled with a purging gas in order to exhaust gas components which may potentially affect the measurements, such as oxygen. Additional disadvantages are that the thick lens can affect the performance of the device. Moreover, the accuracy of the purging gas composition can affect the accuracy of the overall instrument. Finally, the expense of the purging gas is relatively high for operation.

Embodiments of the present invention generally provide a spectroscopic gas sensing apparatus where one or more elements are disposed within an explosion-proof enclosure. The gas sensing apparatus comprises an explosion-proof enclosure that interfaces the measurement path with a light transmitting element. The explosion-proof enclosure contains a light source therein, as well as one or more light sensing components and a suitable gas. The volume of the explosion-proof enclosure is kept relatively small in order to reduce any potential explosion pressure. This relatively small volume, and accordingly small potential explosion pressure, allows the light transmitting element to be thinner than would be required for larger-volume enclosures. This thinner window may interface with potentially hazardous atmospheres since the enclosure is explosion-proof. Accordingly, embodiments of the present invention allow for a volume of suitable gas—with a composition which may stay constant over time—to be positioned between the light source/light sensor and the measurement path. This eliminates undefined gas components or costly purging gases in the light path other than the gas to be measured.

FIG. 1 shows one example of a laser spectroscopy system 100 with which aspects of the present invention are particularly useful. Laser spectroscopy system 100 includes laser 110 that generates laser illumination 112. The emitted light 112 passes through a reference cell 114 and through optical transmission element 116 and through a process area 118 where it reflects off reflective surface 120. After light 112 reflects from reflective surface 120, it travels back through process area 118, element 116 and reference cell 114 where it is received by the detector 111. Device electronics 102 are coupled to detector 111 such that the received light can be detected or otherwise measured. In order to determine the concentration of the gas in the process area 118, the frequency of emitted light 112 has to be precise and known. Device electronics 102, in addition to receiving and responding to user input, can control the wavelength of illumination 112 emitted from laser 110. Laser 110 can be a tunable diode laser that generates the emitted illumination 112 at a set wavelength that is determined either by user input or device electronics 102.

In one example, reference cell 114, through which light 112 passes, contains a known concentration of a fluid with a known absorption value. Process area 118, in one embodiment, is a sample cell.

Figure 2:
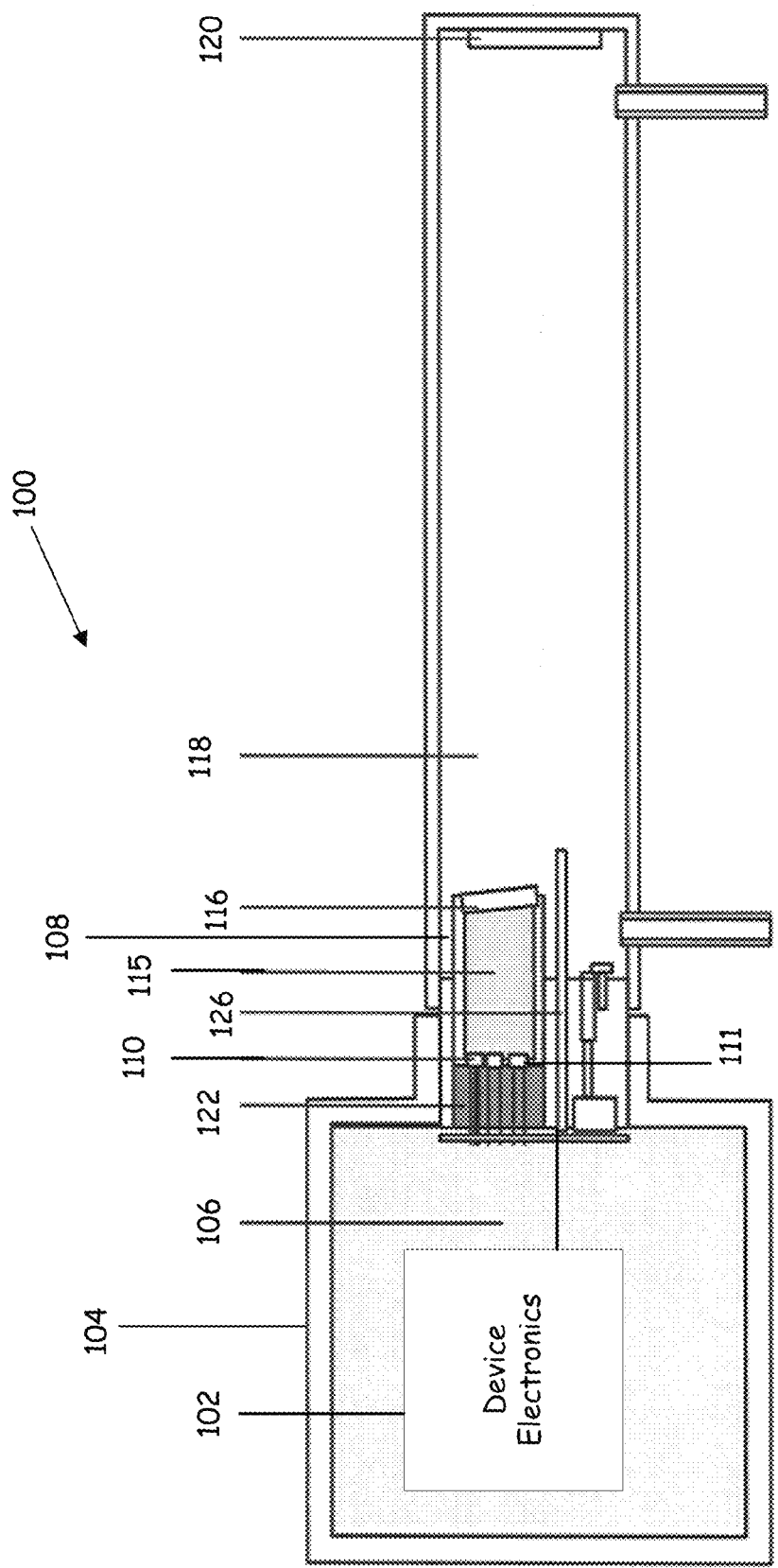
FIG. 2 is a diagrammatic view of an optical gas sensing apparatus with explosion-proof enclosures in accordance with an embodiment of the present invention.

FIG. 2 is a diagrammatic view of an optical gas sensing apparatus with explosion-proof enclosures in accordance with an embodiment of the present invention. Gas sensing apparatus 100 includes device electronics 102 disposed within first explosion-proof enclosure 104. Device electronics 102 can include any suitable electronics including power supply electronics configured to receive power from any suitable source, such as AC power, and condition the power for provision to the various components within device 100. Additionally, device electronics 102 may also include suitable processing circuitry, such as a microprocessor, that is able to suitably control a tunable laser diode and receive outputs from the optical detectors. Based on reception of output signals from the optical detectors, the controller may determine spectral features in the response, and provide an indication of a suitable gas of interest in accordance with known techniques.

In the embodiment illustrated in FIG. 2, enclosure 104 complies with at least one explosion-proof rating, such as that set forth above. Accordingly, if the device electronics 102 were to cause an explosion within enclosure 104, the explosion would not be able to pass outside enclosure 104 and thus would not ignite the ambient environment. In some embodiments, enclosure 104 may be filled, or even pressurized, with a suitable inert gas 106. In order to house device electronics, enclosure 104 may have an internal volume on the order of about 500 $cm^3$ or greater.

In accordance with an embodiment of the present invention, device 100 includes a second explosion-proof enclosure 108 that is smaller than enclosure 104. In one example, the volume of enclosure 108 is about 50 times less than the electronics enclosure. More specifically, the volume of second explosion-proof enclosure 108 is equal to or less than about 10 $cm^3$. By separating sensing enclosure 108 from electronics enclosure 104, the volume of sensing enclosure 108 can thus be kept very small. The energy of an explosion occurring within second explosion-proof enclosure 108 will increase with increased enclosure volume since there will be more explosive gas mixture inside the enclosure. Meanwhile, the internal area of the enclosure on which the energy will act is not increasing at the same rate. For example, the volume of a sphere is proportional to the cube of the radius while the surface area is proportionate to the square of the radius. The pressure acting on the inner walls will therefore be smaller with smaller enclosure volume and thus allow for a thinner window. In embodiments where the volume of second explosion-proof enclosure 108 can be kept at or below 10 $cm^3$, the thickness of light transmitting element can be 3 mm or thinner. This provides significantly improved optical performance.

In the embodiment illustrated in FIG. 2, the only contents within sensing enclosure 108 are light detectors 111, optical light source 110, such as a tunable laser diode, and suitable non-explosive gas 115. Gas 115 within sensing enclosure 108 may remain constant over time to provide a reference for apparatus 100. The light from source 110 is directed through gas 115 inside sensing enclosure 108, through light transmitting element 116 into gas volume 118 and is reflected at reflector 120 back into the sensing enclosure 108 onto one or more light detectors 111.

Apparatus 100 thus allows a controlled gas composition 115 along the complete light path outside the volume of gas 118 to be measured from source 110 to element 116 and from element 116 to one or more light detectors 111. In accordance with an embodiment of the present invention, light transmitting element 116 can be kept thin and will provide improved optical performance over thicker designs. Element 116 can be made thinner because the volume within sensing enclosure 108 is much smaller than that of explosion-proof electronics enclosure 104. Accordingly, any explosion or ignition occurring within sensing enclosure 108 will not reach the pressures that would be possible within electronics enclosure 104. Thus, the thinner design for element 116 is enabled because it need only contain the smaller pressures. Electronics housing 104 and sensing enclosure 108 are coupled together through explosion-rated feed through 122. Feed through 122 is designed in order to be able to withstand explosive pressures within either of enclosures 104 or 108 without allowing the pressure or any flame to propagate to the other enclosure. There are known mounting mechanisms and/or techniques that are configured to withstand explosive pressures and prevent flame propagation from the sensing enclosure into the gas volume to be measured.

Sensing enclosure 108 can have a suitable gas inlet/outlet in order to be periodically filled or evacuated as desired. In one embodiment, enclosure 108 is simply filled and sealed with a pre-defined non-explosive gas or gas mixture. Additionally, or alternatively, the gas in sensing enclosure 108 may be a wavelength reference gas. Finally, one or more additional sensors may be disposed within sensing enclosure 108 while suitable electronics for interacting with such additional sensors may be disposed within electronics enclosure 104. Accordingly, electronic components within electronics enclosure 104 are separated from devices and electronics within sensing enclosure 108. Devices within sensing enclosure 108 are electrically coupled to device electronics 102 via explosion-rated feedthrough 122 illustrated diagrammatically at reference numeral 124. Examples of such additional sensors include, pressure and/or temperature sensors 126 which may also be coupled to device electronics 102 via feed through 122.

Each of enclosures 104 and 108 is designed to comply with at least one explosion-proof rating, such as that set forth above. Accordingly, the measurement path will not be affected by an explosion within either enclosure. Moreover, the enclosure is, in one embodiment, long enough such that the electronic components are protected from the measurement path temperatures which may be outside of the operating range allowed for components within either of enclosures 104, 108. Element 116 is adhered, fused, or otherwise mounted to sensing enclosure 108 with an hermetically tight bond that has high temperature, pressure and chemical resistance. The electronic components within sensing enclosure 108 are, in one embodiment, pre-mounted in cans which, in turn, are adhered or welded onto the housing to ensure gas tightness.

Although the present invention has been described with reference to preferred embodiments, workers skilled in the art will recognize that changes may be made in form and detail without departing from the spirit and scope of the invention.

What is claimed is:

1. An optical gas sensing apparatus comprising:
   a device electronics enclosure constructed in compliance with an explosion-proof rating, the device electronics enclosure housing device electronics;
   a sensing enclosure having a light transmitting element to allow light to pass out of and into the sensing enclosure without significant distortion, the sensing enclosure being operably coupled to the device electronics enclosure by a feed-through, wherein an internal volume of the sensing enclosure is equal to or less than about one fiftieth of a volume of the electronics enclosure, wherein the sensing enclosure is constructed in compliance with the explosion-proof rating;
   a light source disposed within the sensing enclosure and being operably coupled to the device electronics, wherein the device electronics are configured to control a wavelength of illumination emitted by the light source; and
   a detector disposed within the sensing enclosure and being operably coupled to the device electronics.

2. The optical gas sensing apparatus of claim 1, wherein the electronics enclosure is filled with an inert gas.

3. The optical gas sensing apparatus of claim 1, wherein the sensing enclosure is filled with a gas having a known composition.

4. The optical gas sensing apparatus of claim 1, wherein the feed-through is explosion rated.

5. The optical gas sensing apparatus of claim 1, wherein the light source is coupled to the device electronics via the feed-through.

6. The optical gas sensing apparatus of claim 1, wherein the detector s coupled to the device electronics via the feed-through.

7. The optical gas sensing apparatus of claim 1, wherein the electronics enclosure and the sensing enclosure are disposed adjacent one another.

8. The optical gas sensing apparatus of claim 1, and further comprising at least one additional sensor disposed in the sensing enclosure and being operably coupled to the device electronics.

9. The optical gas sensing apparatus of claim 1, wherein the light source is a tunable laser diode.

10. The optical gas sensing apparatus of claim 1, wherein the light transmitting element has a thickness that is selected to comply with an explosion rating.

11. The optical gas sensing apparatus of claim 10, wherein the thickness of the light transmitting element is less than or equal to about 3 millimeters.

12. The optical gas sensing apparatus of claim 1, and further comprising a reflector disposed outside of the sensing enclosure and configured to reflect illumination back into the sensing enclosure through the light transmitting element.

13. The optical gas sensing apparatus of claim 1, wherein the internal volume of the sensing enclosure is less than or equal to about 10 cubic centimeters.

14. An optical gas sensing apparatus comprising:
   an explosion-rated device electronics enclosure, the explosion-rated device electronics enclosure housing device electronics;
   an explosion-rated sensing enclosure having a light transmitting element to allow light to pass out of and into the sensing enclosure, the light transmitting element having a thickness less than or equal to about 3 millimeters, the sensing enclosure being operably coupled to the explosion-rated device electronics enclosure by a feed-through;
   a light source disposed within the sensing enclosure and being operably coupled to, and controlled by, the device electronics;
   a detector disposed within the sensing enclosure and being operably coupled to the device electronics; and
   wherein the explosion-rated device electronics enclosure and the explosion-rated sensing enclosure are both constructed such that each enclosure is configured to retain an internal explosion in compliance with an explosion-proof rating.

15. The optical gas sensing apparatus of claim 14, wherein the electronics enclosure is filled with an inert gas.

16. The optical gas sensing apparatus of claim 14, wherein the sensing enclosure is filled with a gas having a known composition.

17. The optical gas sensing apparatus of claim 14, wherein the feed-through is explosion rated.

18. The optical gas sensing apparatus of claim 14, wherein the light source is coupled to the device electronics via the feed-through.

19. An optical gas sensing apparatus comprising:
   an explosion-rated device electronics enclosure with an enclosure volume, the explosion-rated device electronics enclosure housing device electronics;
   an explosion-rated sensing enclosure, with a sensing volume, the explosion-rated sensing enclosure having a light transmitting element to allow light to pass out of and into the sensing enclosure, the sensing enclosure being operably coupled to the explosion-rated device electronics enclosure by a feed-through, wherein an internal volume of the sensing enclosure is less than or equal to about 10 cubic centimeters;
   a light source disposed within the sensing enclosure and being operably coupled to the device electronics; and
   a detector disposed within the sensing enclosure and being operably coupled to the device electronics;
   wherein the explosion-rated device electronics enclosure and the explosion-rated sensing enclosure are both constructed such that each enclosure is configured to retain an internal explosion and wherein the sensing volume is smaller than the enclosure volume.

20. The optical gas sensing apparatus of claim 19, wherein the sensing volume is at least 10 times smaller than the enclosure volume.

* * * * *

UNITED STATES PATENT AND TRADEMARK OFFICE
CERTIFICATE OF CORRECTION

PATENT NO.        : 9,546,950 B2
APPLICATION NO.   : 14/498309
DATED             : January 17, 2017
INVENTOR(S)       : Peter Schachinger Page 1 of 1

It is certified that error appears in the above-identified patent and that said Letters Patent is hereby corrected as shown below:

In the Claims

Claim 6 Line 51 should recite "the detector is coupled to the device electronics via the"

Claim 7 Line 55 should recite "disposed adjacent to one another."

Signed and Sealed this
Sixth Day of June, 2017

Michelle K. Lee
*Director of the United States Patent and Trademark Office*